United States Patent [19]

Huang et al.

[11] 4,339,606

[45] Jul. 13, 1982

[54] CONVERSION OF KETONES OVER METAL-CONTAINING ZEOLITE CATALYSTS

[75] Inventors: Tracy J. Huang; Werner O. Haag, both of Lawrenceville, N.J.

[73] Assignee: Mobil Oil Corporation, New York, N.Y.

[21] Appl. No.: 232,074

[22] Filed: Feb. 6, 1981

[51] Int. Cl.³ .............................................. C07C 45/45
[52] U.S. Cl. ...................................... 568/396; 568/350
[58] Field of Search ................ 568/396, 350, 353, 390

[56] References Cited

U.S. PATENT DOCUMENTS

| | | | |
|---|---|---|---|
| 2,499,172 | 2/1950 | Smith | 568/396 |
| 3,153,068 | 10/1964 | Porter et al. | 568/396 |
| 3,155,730 | 11/1964 | Eng | 568/396 |
| 3,405,178 | 10/1968 | Wollner et al. | 568/396 |
| 3,574,763 | 4/1971 | Wollner et al. | 568/396 |
| 3,953,517 | 4/1976 | Schmitt et al. | 568/396 |
| 4,146,581 | 3/1979 | Nissen et al. | 568/396 |
| 4,270,006 | 5/1981 | Heilen et al | 568/396 |

FOREIGN PATENT DOCUMENTS

| | | | |
|---|---|---|---|
| 462009 | 9/1976 | Japan | 568/396 |
| 462643 | 3/1977 | Japan | 568/396 |
| 1015003 | 12/1965 | United Kingdom | 568/396 |

Primary Examiner—Natalie Trousof
Assistant Examiner—James H. Reamer
Attorney, Agent, or Firm—Charles A. Huggett; Michael G. Gilman; Claude E. Setliff

[57] ABSTRACT

Ketones are converted in one step to saturated dimeric ketones by passing them over a zeolite having a silica to alumina ratio of at least 12 and a Constraint Index of from 1 to 12 and containing a Group VIII metal.

15 Claims, No Drawings

CONVERSION OF KETONES OVER METAL-CONTAINING ZEOLITE CATALYSTS

BACKGROUND OF THE INVENTION

1. Field of the Invention

The invention relates to a process for making saturated dimeric ketones. More particularly, it relates to making such ketones by using a zeolite catalyst.

2. Discussion of the Prior Art

Currently, commercial processes require three synthesis steps, each with relatively low yield, to convert monomeric ketone, e.g. acetone, to saturated dimeric ketone, e.g. methylisobutyl ketone (MIBK), according to the following schemes:

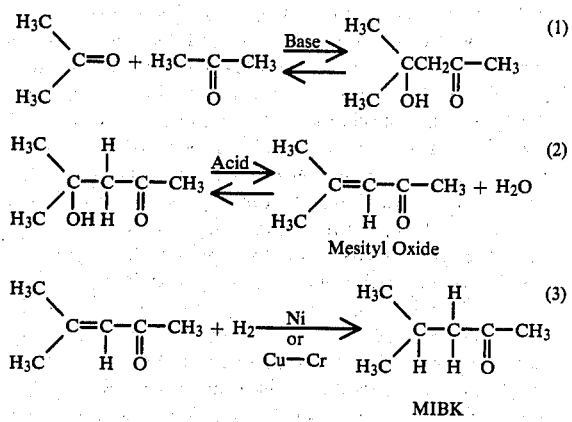

Mesityl oxide is separated from Step (2) and hydrogenated over Ni or Cu-Cr catalyst to form MIBK.

In this synthesis, the following side reactions take place:

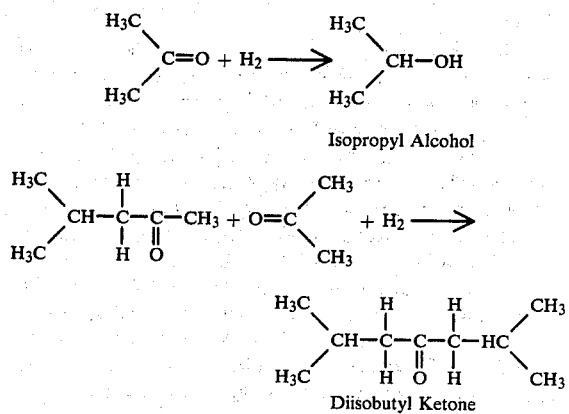

The formation of diisobutyl ketone byproduct is a result of further condensation of MIBK with acetone. Heavier ketones, such as $C_{12}$ ketone, have also been observed in a Pd/resin bifunctional system (see German Pat. No. 1,260,454).

Direct synthesis of methylisobutyl ketone from acetone over bifunction catalysts, such as Pd/zeolite (Japanese Pat. Nos. 46-2009 and 46-2643), Pd/cation exchange resin (German Pat. No. 1,260,454), KOH-alumina-Pd (U.S. Pat. No. 2,499,172), and MgO-silica-Pd (British Pat. No. 1,015,003), has also been reported. The zeolite reported in the Japanese patents is faujasite, which will be shown hereinafter to yield much less of the dimeric ketone, e.g. the MIBK.

U.S. Pat. No. 3,998,898 discloses that acetone can be converted to mesitylene by passing it over an acid catalyst, e.g. an acid zeolite. Note, however, that the patent does not disclose or suggest that a Group VIII metal-containing ZSM-5 or another zeolite as hereinafter defined will selectively yield the dimeric ketone in superior amounts.

SUMMARY OF THE INVENTION

In accordance with the invention, there is provided a process for preparing a saturated dimeric ketone of the formula

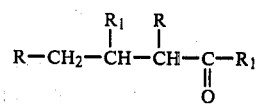

wherein R is hydrogen or a $C_1$–$C_5$ alkyl group and $R_1$ is a $C_1$–$C_6$ alkyl group, R and $R_1$ being the same or different, comprising contacting hydrogen and a ketone of the formula

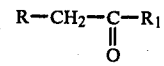

wherein R and $R_1$ are the same or different alkyl groups, as defined hereinabove, with a crystalline zeolite, for example an aluminosilicate zeolite, having a silica to alumina ratio of at least 12 and a Constraint Index of from 1 to 12 and containing a Group VIII metal. The preferred ketone is one in which R is hydrogen and $R_1$ is methyl or ethyl, i.e. dimethyl ketone or methyl ethyl ketone, respectively.

DESCRIPTION OF SPECIFIC EMBODIMENTS

As has been stated, the invention deals with the conversion of a monomeric ketone to a saturated dimeric ketone in one step by contacting hydrogen and the monomeric ketone with a metal-containing zeolite catalyst of the type specified herein, preferably a Pd/ZSM-5. The useful metals are those found in Group VIII of the Periodic Chart of the Elements (the chart copyrighted by Fisher Scientific Company in 1978), e.g. Pd, Pt, Ru, Rh, Ir and Ni.

In one aspect, the zeolites identified herein may be identified in terms of mole ratios of oxides substantially as follows:

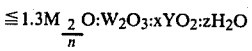

wherein M is a cation, n is the valence of said cation, W is a trivalent metal atom from Groups III through VIII of the Periodic Table or mixtures of such atoms, including, for example, Groups IIIB (e.g., aluminum, gallium, and boron), Group VIA (e.g., chromium) and Group VIII (e.g., iron), Y is silicon or germanium, x is greater than 5 and z is 0 to 40.

Preferably, the mole ratio will be as follows:

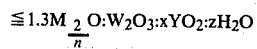

where M, n, W and z are as just defined and x is greater than 12. In a preferred synthesized form, the zeolite has a formula, in terms of mole ratios of oxides, as follows:

$$\leq 1.3 M_{\frac{2}{n}} O : Al_2O_3 : xSiO_2 : zH_2O$$

where M is a mixture of alkali metal cations, especially sodium, and alkylammonium cations, the alkyl groups of which preferably contain from 2 to 5 carbon atoms, and x is greater than 12.

In a preferred embodiment, the zeolite is ZSM-5, W is aluminum, Y is silicon and the silica/alumina ratio is at least 12 and can range up to 4000 or more.

Thus, in general the term "zeolite" herein defines a natural or synthetic porous tectosilicate characterized by having a rigid crystalline framework structure composed of an assembly of silicon atoms and at least a trace amount of a trivalent metal atom, preferably aluminum, but which can also be iron, boron, gallium, chromium, and the like, or mixtures thereof, the silicon atoms and trivalent metal atoms each being surrounding by a tetrahedron of shared oxygen atoms, and a precisely defined pore structure.

The crystalline zeolites utilized herein are more particularly members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 1600 and above.

In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal area formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reaons and, therefore, it is not the present invention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10 percent and 60 percent. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60 percent for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10 percent.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

TABLE 1

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. No. 3,702,886 and U.S. Pat. No. Re 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

$$(0-15)RN:(0-1.5)M_{2/n}O:(0-2)AL_2O_3:(100)SiO_2$$

wherein:
M is at least one cation having a valence n; and
RN is a $C_1$–$C_{20}$ organic compound having at least one amine functional group of $pK_a \geq 7$.

It is recognized that, particularly when the composition contains tetrahedral, framework aluminum, a fraction of the amine functional groups may be protonated. The doubly protonated form, in conventional notation, would be $(RNH)_2O$ and is equivalent in stoichiometry to $2RN + H_2O$.

The characteristic X-ray diffraction pattern of the synthetic zeolite ZSM-48 has the following significant lines:

TABLE 2

| Characteristic Lines of ZSM-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, $100 \, I/I_o$, where $I_o$ is the intensity of the strongest line or peak, and d (obs.), the interplanar spacing in A, corresponding to the recorded lines, were calculated. In the foregoing table the relative intensities are given in terms of the symbols W=weak, VS=very strong and W-S=weak-to-strong. Ion exchange of the sodium with cations reveals substanitally the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

TABLE 3

| REACTANTS | BROAD | PREFERRED |
|---|---|---|
| $Al_2O_3/SiO_2$ | = 0 to 0.02 | 0 to 0.01 |
| $Na/SiO_2$ | = 0 to 2 | 0.1 to 1.0 |
| $RN/SiO_2$ | = 0.01 to 2.0 | 0.05 to 1.0 |
| $OH^-/SiO_2$ | = 0 to 0.25 | 0 to 0.1 |
| $H_2O/SiO_2$ | = 10 to 100 | 20 to 70 |
| $H^+$(added)/$SiO_2$ | = 0 to 0.2 | 0 to 0.05 | wherein RN is a $C_1$-$C_{20}$ organic compound having amine functional group of $pK_a \geq 7$. The mixture is maintained at 80°–250° C. until crystals of the material are formed. $H^+$(added) is moles acid added in excess of the moles of hydroxide added. In calculating $H^+$ (added) and OH values, the term acid ($H^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$-$C_{20}$ organic compound containing at least one amine functional group of $pK_a \geq 7$, as defined above, and includes such compounds as $C_3$-$C_{18}$ primary, secondary, and tertiary amines, cyclic amine (such as piperidine, pyrrolidine and piperazine), and polyamines such as $NH_2$—$C_nH_{2n}$—$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal stucture, as identified by the X-ray diffraction "fingerprint", which establishes the identity of the specific crystalline zeolite material.

The specified zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article Zeolite Structure by W. M. Meier. This paper, the entire contents of which are incorporated herein by reference, is included in Proceedings of the Conference on Molecular Sieves, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

TABLE 4

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

Useful ketones, in addition to those specifically named in the "Summary", include methylbutyl ketone, methylhexyl ketone, diethyl ketone, dipropyl ketone, butyl hexyl ketone, amylhexyl ketone and the like. It will be understood that this specific disclosure includes all the possible combinations of R and $R_1$, as defined hereinabove.

The process is carried out at a temperature of from about 100° C. to about 350° C., at a pressure of from about 0 to about 2000 psig, with a contact time sufficient to achieve the desired degree of ketone conversion. If contacting is carried out, as is preferred, in a fixed bed flow reactor, the weight hourly space velocity (WHSV) is from about 0.2 to about 20. The metal content of the catalyst is in the range of from about 0.01 to 2.0 wt. percent, preferably from about 0.05 to about 0.5 wt. percent. The metal incorporation can be carried out either by impregnation or ion exchange. Alternatively, a physical mixture of zeolite and metal catalyst components can be used. The hydrogen/ketone ratio can vary from about 0.1 to about 5.0. The preferred process conditions are: temperature, from about 150° C. to about 240° C.; pressure, from about 400 to about 1000 psig; WHSV, from about 1 to about 8; and $H_2$ ketone mole ratio from about 0.4 to about 1.0.

As has been stated, the zeolites used in this invention may have the original cations associated therewith wholly or partly replaced by a wide variety of other cations according to techniques well known in the art, as by ion exchange. Typical replacing cations include hydrogen, ammonium, and metal cations including mixtures of the same. Of the replacing cations, particular preference is given to cations of hydrogen, alkali, ammonium, rare earth, magnesium, calcium, zinc, copper, silver, platinum, palladium, nickel and mixtures thereof. The metals may be also added by impregnation.

Typical ion exchange techniques include contacting the particular zeolite with a salt of the desired replacing cation or cations. Although a wide variety of salts can be employed, particular preference is given to chlorides, nitrates and sulfates. Pd and Pt can also be exchanged via their tetramine complex ions.

Representative ion exchange techniques are disclosed in a wide variety of patents, including U.S. Pat. Nos. 3,140,249; 3,140,251; and 3,140,253.

Following contact with the salt solution of the desired replacing cation, the zeolites may be washed with water and dried at a temperature ranging from 150° F. to about 600° F. and thereafter may be heated in air or other inert gas at temperatures ranging from about 500° F. to 1700° F. for periods of time ranging from 1 to 48 hours or more.

The following examples will illustrate the invention. It will be understood that they are illustrative only and are not meant to limit the invention.

EXAMPLE 1

In this Example, the single-step synthesis is carried out in the presence of hydrogen over a bifunctional Pd/ZSM-5 to yield MIBK directly, as follows:

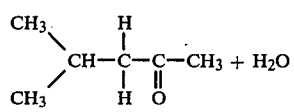

A sample of ZSM-5 containing 0.5 percent by weight of Pd was placed in a stainless steel reactor and the unit was pressurized with helium to 600 psig and heated to 180° C. After the desired temperature was reached, acetone, together with hydrogen, was fed into the reactor at a $H_2$/acetone mole ratio of 0.6 and an acetone weight hourly space velocity (WHSV) of 3.8. The conversion was conducted in a fixed-bed reactor in downflow fashion. The products were collected and analyzed by gas chromatography. The results (see Table 5) showed that acetone conversion was 28.5 wt. percent and MIBK selectivity was 98.3 wt. percent.

EXAMPLE 2

The experiment was made in exactly the same as in Example 1, except that a sample of REY (rare earth-containing faujasite Y) containing 0.35 percent Pd was used. As shown in Table 5, Pd/REY gave only 30 wt. percent MIBK selectivity with an acetone conversion of 29.4 wt. percent.

TABLE 5

| ACETONE CONVERSION | | |
|---|---|---|
| | Example 1 | Example 2 |
| Catalyst | Pd/ZSM-5 | Pd/REY |
| Temperature | 180° C. | 180° C. |
| Pressure | 600 psig | 600 psig |
| WHSV (Acetone) | 3.8 | 3.8 |
| $H_2$/Acetone (mole ratio) | 0.6 | 0.6 |
| Reactor Effluent, wt. percent | | |
| Diisopropyl Ether | — | 3.6 |
| Acetone | 71.5 | 70.6 |
| Isopropyl Alcohol | 0.4 | 14.2 |
| Mesityl Oxide | — | 0.1 |
| MIBK | 23.8 | 8.1 |
| $C_9$ Ketones* | — | 1.0 |
| Water | 4.3 | 2.4 |
| Acetone Conversion, wt. percent | 28.5 | 29.4 |
| Product Selectivity, **wt. percent | | |
| Diisopropyl Ether | — | 13.3 |
| Isopropyl Alcohol | 1.7 | 52.6 |
| Mesityl Oxide | — | 0.4 |
| MIBK | 98.3 | 30.0 |
| $C_9$ Ketones* | — | 3.7 |

*Mainly diisobutyl ketone
**Excluding water

From the comparison in Table 5, it is clearly demonstrated that Pd/ZSM-5 gives a MIBK selectivity advantage over Pd/REY. As can be seen further, the Pd/ZSM-5 catalyst produces no diisobutyl ketone.

We claim:

1. A process for preparing a saturated dimeric ketone of the formula

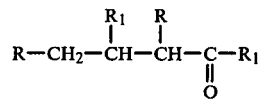

wherein R is hydrogen or a $C_1$–$C_5$ group and $R_1$ is a $C_1$–$C_6$ alkyl group, R and $R_1$ being the same or different, comprising contacting a hydrogen and a ketone of the formula

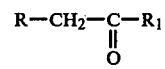

wherein R and $R_1$ are as hereinbefore defined, with a crystalline zeolite having a silica to alumina ratio of at least 12 and a Constraint Index of from 1 to 12 and containing a Group VIII metal incorporated by exchange, impregnation or physical admixture, the process being carried out at from about 100° C. to about 300° C., at a pressure of from 0 to about 2000 psig and a weight hourly space velocity of from about 0.2 to about 20.

2. The process of claim 1 wherein the feed is acetone and the product is methylisobutyl ketone.

3. The process of claim 1 wherein the Group VIII metal is palladium.

4. The process of claim 1 wherein the metal content of the catalyst is in the range of about 0.01 to about 2.0 wt/percent.

5. The process of claim 3 wherein the palladium is incorporated by impregnation.

6. The process of claim 3 wherein the palladium is incorporated by ion exchange.

7. The process of claim 1 wherein the catalyst is a physical mixture of HZSM-5 and a supported palladium catalyst.

8. The process of claim 1 wherein the temperature range is from about 150° C. to about 240° C.

9. The process of claim 1 wherein the pressure range is from about 400 to about 1000 psig.

10. The process of claim 1 wherein the weight hourly space velocity is from about 1 to about 8.

11. The process of claim 1 wherein the $H_2$/ketone mole ratio is from about 0.4 to about 1.0.

12. The process of claim 1 wherein said zeolite is an aluminosilicate zeolite.

13. The process of claim 1 wherein said zeolite is ZSM-5.

14. The process of claim 1 wherein the zeolite has the formula, in terms of mole ratios of oxides, $$1.3 M_2:W_2O_3:xYO_2:zH_2O$$

wherein M is a cation selected from the group consisting of alkylammonium, a metal from Group I of the Periodic Table, and mixtures thereof, W is a trivalent cation selected from one of the Groups III through VIII of the Periodic Table, Y is silicon or germanium, n is the valence of M, x is at least 12 and z is 0 to 40.

15. The process of claim 14 wherein M is a Group VIII metal cation, W is aluminum, gallium, boron, chromium or iron and Y is silicon.

* * * * *

UNITED STATES PATENT AND TRADEMARK OFFICE
CERTIFICATE OF CORRECTION

PATENT NO. : 4,339,606
DATED : July 13, 1982
INVENTOR(S) : TRACY J. HUANG and WERNER O. HAAG It is certified that error appears in the above-identified patent and that said Letters Patent are hereby corrected as shown below:

Column 6, line 36, "...(0-2)AL$_2$O$_3$..." should be --...(0-2)Al$_2$O$_3$--.

Column 13, Claim 14 formula, "1.3M$_2$:W..." should be --1.3M$_2$O:W...--.

Signed and Sealed this

Eighteenth Day of January 1983

[SEAL]

Attest:

GERALD J. MOSSINGHOFF

Attesting Officer    Commissioner of Patents and Trademarks